US006489483B1

(12) United States Patent
Suda et al.

(10) Patent No.: US 6,489,483 B1
(45) Date of Patent: Dec. 3, 2002

(54) PROCESS FOR THE PRODUCTION OF 2-PYRIDYLPYRIDINE DERIVATIVES

(75) Inventors: Hirokazu Suda, Kanagawa (JP); Ken Umihara, Kanagawa (JP)

(73) Assignee: Sankio Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/009,479

(22) PCT Filed: Jun. 13, 2000

(86) PCT No.: PCT/JP00/03832

§ 371 (c)(1),
(2), (4) Date: Dec. 13, 2001

(87) PCT Pub. No.: WO00/76976

PCT Pub. Date: Dec. 21, 2000

(30) Foreign Application Priority Data

Jun. 14, 1999  (JP) .......................................... 11-167309

(51) Int. Cl.[7] ............................................. C07D 213/22
(52) U.S. Cl. ....................................... 546/257; 546/258
(58) Field of Search .................................. 546/257, 258

(56) References Cited

U.S. PATENT DOCUMENTS 4,149,002 A    4/1979   Beschke et al.
4,966,972 A    10/1990  Goe et al.

FOREIGN PATENT DOCUMENTS

JP      64-3169       1/1989
WO      WO 99/15503   4/1999

OTHER PUBLICATIONS

XP–001071276—"Functionalization of 2,2'–bipyridines in Their 4 and 5 Positions. Synthesis of 5–Ethynyl–2,2'–bipyridine", vol. 3, pp. 321–324 (Mar. 1988).
Malm, et al. "Palladium–Catalyzed Coupling of Heteroaryl Alkystannanes with Heteroaryl Halides in the Presence of Silver (I) oxide." Tetrahedron Letters., vol. 33, No. 16, p. 2199–2202 (1992).
Ishikura, et al. "A Novel Synthesis of 4–Aryl– and 4–Heteroarylpyridines via Diethyl (4–pyridyl) borane."Chemical & Pharmaceutical Bulletin., vol. 33, No. 11, p. 4755–4763 (1985).
International Search Report.

*Primary Examiner*—Patricia L. Morris
(74) *Attorney, Agent, or Firm*—Sughrue Mion, PLLC

(57) ABSTRACT

A process for producing a 2-pyridylpyridine derivative usable as an intermediate for medicines or agricultural chemicals is provided, which does not require expensive special catalysts and special equipment, which does not cause environmental problems, and which can be conducted on an industiral scale. The process comprises reacting an acetyl-substituted pyridine derivative with a 3-amino acrolein, then reacting the reaction product with ammonia or an ammonium salt.

9 Claims, No Drawings

PROCESS FOR THE PRODUCTION OF 2-PYRIDYLPYRIDINE DERIVATIVES

TECHNICAL FIELD

This invention provides a process for producing a 2-pyridylpyridine derivative, an important intermediate for producing medicines, agricultural chemicals, catalyst ligands, organic electroluminescence elements, charge transfer materials, electrophotographic photo-sensitive materials and dyes, in a high yield and with a high purity in a sequential manner at a low production cost, which process can be conducted on an industiral scale.

BACKGROUND ART

As reactions for synthesizing 2-pyridylpyridine derivatives, there have conventionally been known Ullmann reaction between 2-bromopyridine and 4-chloropyridine in nitrobenzene (Khim. Geol. Nauk., 114 (1970)), a reaction utilizinga cobalt catalyst (Synthesis, 600 (1975); Chem. Pharm. Bull., 33, 4755 (1985)), a coupling reaction between an alkyltin derivative and a halogenated pyridine in the presence of a Pd catalyst (Tetrahedron Lett., 33, 2199 (1992)), and a coupling reaction of halogenated pyridine derivatives with each other (W09852922). These reactions, however, involve many problems. For example, they require extremely expensive catalysts or reagents, require a special treatment for metal-containing waste liquor, and require difficult separation of by-products produced therefrom, thus not being said to be industrially advantageous techniques.

In addition, there have been proposed a cross-coupling reaction utilizing Grignard reaction (Japanese Patent Laid-Open No. 3169/1989; Tetrahedron Lett., 28, 5845 (1987) and synthesis by Wurtz reaction of halogenated pyridine derivatives with each other in the presence of Li metal under irradiation with ultrasonic waves (Tetrahedron Lett., 30, 3567 (1989); Synthesis, 564 (1986)). However, these reactions require exclusive equipment, and involve many problems for production on a large scale.

Recently, it has been reported to form a pyridine ring via pyridinium ion by iodinating an acetylpyridine derivative (Synthesis., 815 (1999)). This technique causes environmental problems since it involves halogenation and, in case where iodine used in the iodination remains, by-products are produced in the subsequent step. Thus, a purification step must be provided before the step after the iodination, which is not advantageous for synthesis on a large scale.

The present invention provides a process for producing a 2-pyridylpyridine derivative usable as an intermediate for medicines or agricultural chemicals, which does not require expensive special catalysts and special equipment, which does not cause environmental problems, and which can be conducted on an industrial scale and, more particularly, provides a process for producing a 2-pyridylpyridine derivative with a high positional specificity and a high purity in a high yield, which enables to produce the 2-pyridylpyridine derivative in a sequential manner at a low production cost.

DISCLOSURE OF THE INVENTION

The objects of the invention can be attained by the following processes. That is:

(1) a process for producing a 2-pyridylpyridine derivative, which comprises reacting an acetyl-substituted pyridine derivative with a 3-aminoacrolein, then reacting the reaction product with ammonia or an ammonium salt;

(2) a process for producing a 2-pyridylpyridine derivative as described in (1) above, wherein the acetyl-substituted pyridine derivative is a compound represented by the following general formula (I):

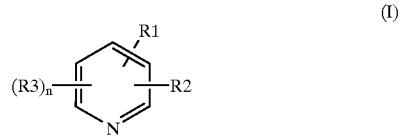

wherein R1 and R2 each independently represent a hydrogen atom, a halogen atom, an alkyl group, a heterocyclic group or an aryl group or, when taken together, R1 and R2 may form a ring, R3 represents an acetyl group, and n represents an integer of 1 to 3;

(3) a process for producing a 2-pyridylpyridine derivative as described in (1) above, wherein the ammonium salt is ammonium chloride, ammonium acetate or ammonium formate;

(4) a process for producing a 2-pyridylpyridine derivative as described in (1) above, wherein amount of the ammonia or the ammonium salt to be used is 1 to 30 mols per mol of the acetyl-substituted pyridine derivative;

(5) a process for producing a 2-pyridylpyridine derivative as described in (1) above, wherein the acetyl-substituted pyridine derivative and the 3-aminoacrolein are reacted with each other in the presence of a base;

(6) a process for producing a 2-pyridylpyridine derivative as described in (5) above, wherein amount of the base to be used is 0.1 to 10 mols per mol of the acetyl-substituted pyridine derivative;

(7) a process for producing a 2-pyridylpyridine derivative as described in (1) above, wherein an acid catalyst is used in the reaction between the reaction product of the acetyl-substituted pyridine with the 3-aminoacrolein and ammonia or the ammonium salt;

(8) a process for producing a 2-pyridylpyridine derivative as described in (7) above, wherein the acid is formic acid, ac acid or propionic acid; and (9) a process for producing a 2-pyridylpyridine derivative as described in (1) above, wherein a solvent is used in the reaction between the acetyl-substituted pyridine derivative and the 3-aminoacrolein.

The invention is described in more detail below.

In order to describe the invention in more detail, one embodiment of the process of the invention is shown below which, however, does not limit the invention in any way.

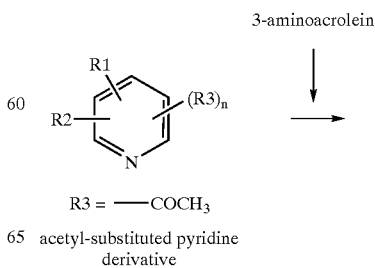

acetyl-substituted pyridine derivative

-continued

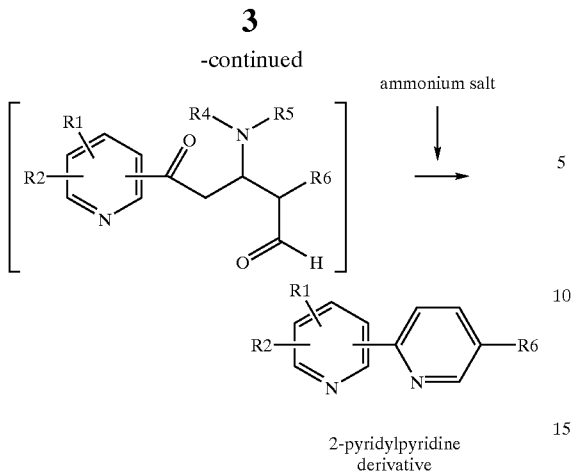

2-pyridylpyridine
derivative

In the invention, the acetyl-substituted pyridine derivative is exemplified by the compounds represented by the following general formula (I). The 3-aminoacrolein is exemplified by those 3-aminoacroleins which are represented by the following general formula (II) or (III). However, these are not to be construed to limit the scope of the invention.

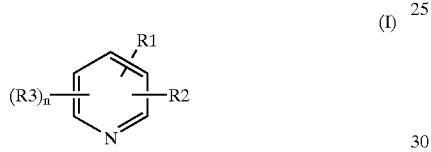
(I)

In the above general formula (I), R1 and R2 each independently represents a hydrogen atom, a halogen atom, an alkyl group, a heterocyclic group or an aryl group or, when taken together, R1 and R2 may form a ring, R3 represents an acetyl group, and n represents an integer of 1 to 3. In the above embodiment of the process of the invention, n=1.

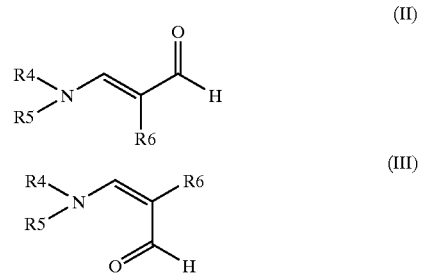
(II)

(III)

In the above formula (II) or (III), R4 and R5 each independently represent an alkyl group or, when taken together, R4 and R5 may form a ring, and R6 represents a hydrogen atom, a halogen atom or an alkyl group.

In the above general formulae (I) to (III), the alkyl group includes amethyl group, an ethyl group and a propyl group, with methyl group being preferred. The aryl group includes aphenyl group. The heterocyclic group includes a pyridyl group and a pyrazyl group, with pyridyl group being preferred. The halogen atom includes a fluorine atom, a chlorine atom and a bromine atom, with fluorine atom and chlorine atom being preferred. The ring formed by R1 and R2 includes a benzene ring and a cyclohexane ring, with benzene ring being preferred.

The ring formed by R4 and R5 includes a piperidine ring, a pyrrolidine ring and a morpholine ring, with morpholine ring being preferred.

As the acetyl-substituted pyridine derivatives to be used in the invention, there are specifically illustrated following compounds (IV-1) to (IV-6) including those represented by the above general formula (I). In the following formulae, R7 represents an acetyl group.

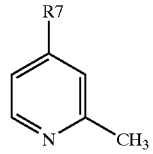
(IV-1)

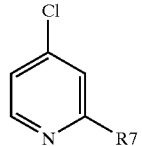
(IV-2)

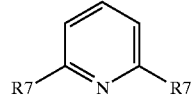
(IV-3)

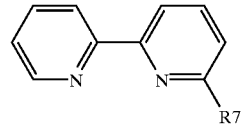
(IV-4)

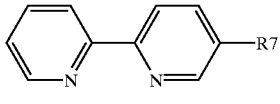
(IV-5)

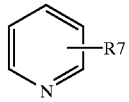
(IV-6)

These acetyl-substituted pyridine derivatives may be obtained from, for example, easily available compounds wherein R7 represents a cyano group, by reacting them with a Grignard reagent (MeMgI) prepared from methyl iodide according to the process described in Org. Syntheses., Coll. Vol. III, 26(1965), then hydrolyzing the product to thereby convert R7 to acetyl group.

In the invention, no reaction solvents may be used throughout the all steps but, if necessary, there may be used any of polar or non-polar organic solvents such as aromatic solvents, e.g., benzene, toluene, xylene, chlorobenzene and dichlorobenzene; polar solvents, e.g., pyridine, acetonitrile, N,N-dimethylformamide, N,N-dimethylacetamide and N-methylpyrrolidone; ester solvents, e.g., methyl acetate, ethyl acetate and butyl acetate; and alcohols, e.g., methanol, ethanol, isopropyl alcohol, butanol and t-butanol. Preferred solvents are ether solvents such as diethyl ether, diisopropyl ether, dibutyl ether, methyl t-butyl ether and tetrahydrofuran (abbreviated as "THF"), with THF being more preferred. In addition, two or more of these solvents maybe used as a mixture, with the mixing ratio being freely determined. The reaction solvent is used in an amount of 1 to 50 parts by weight per part by weight of the acetyl-substituted pyridine derivative, with an amount of 2 to 30 parts by weight being more preferred and an amount of 4 to 8parts by weight being still more preferred.

In the invention, existence of a base is preferred in reacting the acetyl-substituted pyridine with the 3-aminoacrolein. As the base to be used in the invention, any base maybe used and, usually, metal alkoxides such as potassium t-butoxide, sodium t-butoxide and sodium ethoxide, inorganic bases such as sodium hydride, metallic sodium, sodium hydroxide and potassium hydroxide, and organic bases such as triethylamine and diisopropylamine may be used. Of these, potassium t-butoxide, sodium t-butoxide and sodium hydride are preferred, with potassium t-butoxide being more preferred. These bases are used in an amount of 0.1 to 10 mols, preferably 0.8 to 2.0 mols, more preferably 0.9 to 1.2 mols, per mol of the acetyl-substituted pyridine derivative.

Ammonia or the ammonium salts to be used in the invention maybe in any form but, usually, an ammonia gas, aqueous ammonia, ammonium chloride, ammonium acetate or ammonium formate is used. Of these, ammonium chloride, ammonium acetate and ammonium formate are preferably used, with ammonium acetate being more preferred. These are used in an amount of 1 to 30 mols, preferably 3 to 15 mols, more preferably 6 to 10 mols, per mol of the acetyl-substituted pyridine derivative. Two or more different forms of ammonia may be mixed to use, with the mixing ratio being freely determined.

In the invention, reaction temperature upon reacting the acetyl-substituted pyridine derivative with the 3-aminoacrolein ranges from 20 to 100° C., preferably from 40 to 80° C., more preferably from 40 to 60° C. Reaction temperature upon subsequently reacting the reaction product with ammonia or the ammonium salt ranges from 40 to 200° C., preferably from 50 to 150° C., more preferably from 60 to 120° C. These reactions complete usually within 24 hours and, in many cases, disappearance of the starting materials is confirmed in 5 to 12 hours.

In the process of the invention, catalysts are not particularly required throughout the all steps. However, in the reaction between the reaction product of the acetyl-substituted pyridine derivative with the 3-aminoacrolein and ammonia or the ammonium salt, use of an acid catalyst serves to complete the reaction in a shorter period of time, thus being preferred. As such acid catalyst, any acid may be used and, specifically, there may be used in organic acids such as sulfuric acid and hydrochloric acid, organic acids such as p-toluenesulfonic acid, formic acid, acetic acid and propionic acid, and strongly acidic ion-exchange resins such as Amberlite and Amberlyst. Preferably, formic acid, acetic acid or propionic acid capable of keeping the reaction system weakly acidic is used, with acetic acid being more preferred.

After completion of the reaction, the end product of 2-pyridylpyridine derivative is purified by recrystallization from alcohol, hexane or toluene, column purification using silica gel or distillation under reduced pressure. These purification methods may be employed independently or in combination of two or more to obtain the end product with a high purity.

BEST MODE FOR CARRYING OUT THE INVENTION

The invention is now described more specifically by reference to Examples which, however, are not to be construed as limiting the invention. Additionally, purity was determined by high pressure liquid chromatography (abbreviated as "HPLC"). Chemical structures of the end products synthesized in Examples are shown below.

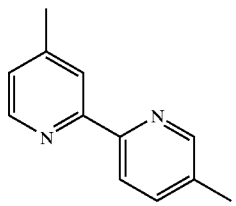

(V)

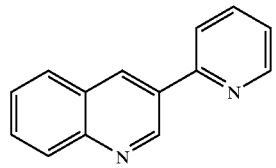

(VI)

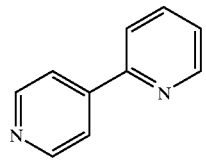

(VII)

EXAMPLE 1

Synthesis of 4,4'-dimethyl-2,2'-dipyridyl (V)

4.06 g (0.030 mol) of 4-methyl-2-acetylpyridine and 3.56 g (0.032 mol) of 2-methyl-3-dimethylaminopropenal were dissolved in 40 ml of tetrahydrofuran, 3.63 g (0.032 mol) of potassiumt-butoxidewas added, and heated at 60° C. for 30 minutes. To this mixture solution were added 23.12 g (0.30 mol) of ammonium acetate and 30 ml of acetic acid and, after allowing to react at 60° C. for 2 hours, the internal temperature was raised up to 105° C. to remove tetrahydrofuran, followed by allowing to react at 105° C. for 2 hours. After the reaction solution was allowed to cool, 80 ml of a 25% NaOH aqueous solution was added, then extracted with 4×100 ml ethyl acetate. The organic layer was dried over anhydrous sodium sulfate, filtered, and concentrated. Toluene was added to the concentrate to recrystallize, thus 3.30 g (yield: 59.7%) of pale yellow powder being obtained. HPLC analysis (column: ODS-80TM; detecting UV: 254 nm; flow rate: 1.0 ml/min; eluant: methanol/water= 40/60; buffer: triethylamine 0.1%, acetic acid 0.1%) revealed that purity of the product was 98.0%, melting point: 170° C. to 172° C.

EXAMPLE 2

Synthesis of 3-(2-pyridyl) quinoline (VI)

5.14 g (0.030 mol) of 3-acetyl quinoline and 3.12 g (0.031 mol) of 3-dimethylaminopropenal were dissolved in 35 ml of tetrahydrofuran, 3.64 g (0.032 mol) of potassium t-butoxide was added, and heated at 60° C. for 10 minutes. Subsequently, 18.50 g (0.24 mol) of ammonium acetate and 14 ml of acetic acid were added and, after allowing to react at 60° C. for 2 hours, the internal temperature was raised up to 105° C. to remove tetrahydrofuran, followed by allowing to react at 105° C. for 2 hours. After the reaction solution was allowed to cool, 60 ml of a 25% NaOH aqueous solution was added, then the mixture was extracted with 4×100 ml ethyl acetate. The organic layer was dried over anhydrous sodium sulfate, filtered, and concentrated. The concentrate was distilled under reduced pressure (bp. 165 to 170° C./0.1 Torr) to obtain 2.88 g (yield: 56.0%) of pale yellow liquid. HPLC analysis (column: ODS-80TM; detecting UV: 264 nm; flow rate: 1.0 ml/min; eluant: acetonitrile/water=82/18; buffer: triethylamine 0.1%, acetic acid 0.1%) revealed that purity of the product was 98.7%, boiling point: 165° C. to 170° C.

EXAMPLE 3

Synthesis of 2,4'-dipyridyl (VII)

2.91 g (0.024 mol) of 4-acetylpyridine and 2.97 g (0.030 mol) of 3-dimethylaminopropenal were dissolved in 100 ml of THF, 2.69 g (0.024 mol) of potassium t-butoxide was added, and heated at 60° C. for 10 minutes. Subsequently, 23.12 g (0.30 mol) of ammonium acetate and 60 ml of acetic acid were added and, after allowing to react at 60° C. for 3.5 hours, THF was removed in an evaporator. Then, 100 ml of water and 150 ml of a 25% NaOH aqueous solution were added, and the mixture was extracted with 4×100 ml ethyl acetate. The organic layer was dried over anhydrous sodium sulfate, concentrated under A reduced pressure, and recrystallized from hexane to obtain 1.92 g (yield: 51.2%) of colorless platy crystals. HPLC analysis (column: ODS-80TM; detecting UV: 264 nm; flow rate: 1.0 ml/min; eluant: acetonitrile/water=50/50; buffer: triethylamine 0.1%, acetic acid 0. 1%) revealed that purity of the product was 99.3%, melting point: 55.8° C. to 56.0° C.

COMPARATIVE EXAMPLE 1

Example of synthesizing 2,4'-dipyridyl (VII) shown in Example 3 was compared with the following synthesizing process (Table 1). Comparative Example 1 shows synthesis by Ullmann reaction between 2-bromopyridine (X) and 4-chloropyridine (XI) (Khim. Geol. Nauk., 114 (1970)). Although this process enables to synthesize by the reaction between comparatively simple compounds, selectivity of the end product is low and, in comparison with Example 3 of the invention, selectivity in Example 3 is clearly higher than in the Comparative Example Table 1.

TABLE 1

| | Synthesis Condition | By-product VIII | IX | End Product VII |
|---|---|---|---|---|
| Comparative Example 1 | Ullmann reaction between X and XI | 57.2% | 12.5% | 14.5% |
| Example 3 | described | not detected by HPLC | not detected by HPLC | 51.2% |

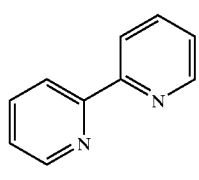

(VIII)

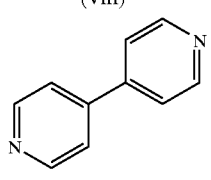

(IX)

TABLE 1-continued

| | Synthesis Condition | By-product VIII | IX | End Product VII |
|---|---|---|---|---|

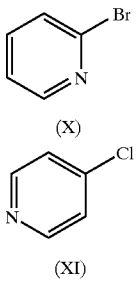

(X)

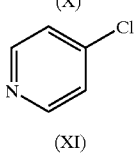

(XI)

INDUSTRIAL APPLICABILITY

As is apparent from the above examples and comparative example, the invention provides a process for producing a 2-pyridylpyridine derivative usable as an intermediate for medicines or agricultural chemicals, which does not require expensive special catalysts and special equipment, which does not cause environmental problems, and which can be conducted on an industrial scale, more particularly, a process for producing a 2-pyridylpyridine derivative with a high positional specificity and a high purity in a high yield, which enables to produce in a sequential manner at a low production cost.

What is claimed is:

1. A process for producing a 2-pyridylpyridine derivative, which comprises reacting an acetyl-substituted pyridine derivative with a 3-aminoacrolein, then reacting the reaction product with an ammonia or an ammonium salt.

2. The process for producing a 2-pyridylpyridine derivative as described in claim 1, wherein the acetyl-substituted pyridine derivative is a compound represented by formula (I):

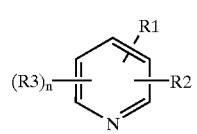

(I)

wherein R1 and R2 each independently represents a hydrogen atom, a halogen atom, an alkyl group, a heterocyclic group or an aryl group; when taken together, R1 and R2 may form a ring; R3 represents an acetyl group; and n represents an integer of 1 to 3.

3. The process for producing a 2-pyridylpyridine derivative as described in claim 1, wherein the ammonium salt is an ammonium chloride, an ammonium acetate or an ammonium formate.

4. The process for producing a 2-pyridylpyridine derivative as described in claim 1, wherein an amount of the ammonia or the ammonium salt to be used is 1 to 30 mol per mol of the acetyl-substituted pyridine derivative.

5. The process for producing a 2-pyridylpyridine derivative as described in claim 1, wherein the acetyl-substituted pyridine derivative is reacted with the 3-aminoacrolein in the presence of a base.

6. The process for producing a 2-pyridylpyridine derivative as described in claim 5, wherein an amount of the base to be used is 0.1 to 10 mol per mol of the acetyl-substituted pyridine derivative.

7. The process for producing a 2-pyridylpyridine derivative as described in claim 1, wherein an acid catalyst is used in the reaction between the ammonia or the ammonium salt and the reaction product of the acetyl-substitutedpyridine with the 3-aminoacrolein.

8. The process for producing a 2-pyridylpyridine derivative as described in claim 7, wherein the acid catalyst is a formic acid, an acetic acid or a propionic acid.

9. The process for producing a 2-pyridylpyridine derivative as described in claim 1, wherein a solvent is used in the reaction between the acetyl-substituted pyridine derivative and the 3-aminoacrolein.

\* \* \* \* \*